United States Patent [19]

Levy

[11] Patent Number: 4,754,058

[45] Date of Patent: Jun. 28, 1988

[54] INHIBITION OF POLYMERIZATION FOULING DURING DISTILLATION OF MONOMERS IN THE PRESENCE OF SULFUR OXIDES

[75] Inventor: Leon B. Levy, Corpus Christi, Tex.

[73] Assignee: Hoechst Celanese Corporation, North Somerville, N.J.

[21] Appl. No.: 57,480

[22] Filed: Jun. 2, 1987

[51] Int. Cl.$^4$ ............................................. C07C 69/52
[52] U.S. Cl. ....................................... 560/205; 203/8; 203/DIG. 1
[58] Field of Search ............ 560/205; 203/8, DIG. 21

[56] References Cited

U.S. PATENT DOCUMENTS

| | | | |
|---|---|---|---|
| 2,741,583 | 8/1956 | Vaughan et al. | 560/205 |
| 3,539,621 | 11/1970 | Cipollone et al. | 560/205 |
| 3,894,076 | 7/1975 | Van Duyne et al. | 560/205 |
| 3,964,979 | 6/1976 | Watson | 203/9 |
| 4,338,162 | 7/1982 | Johnson | 203/8 |

*Primary Examiner*—Paul J. Killos
*Attorney, Agent, or Firm*—William E. O'Brien

[57] ABSTRACT

Polymer formation is inhibited during the distillation of ethyl acrylate and acrylic acid produced from the reaction of ethylene and acrylic acid with sulfuric acid. In the presence of sulfur dioxide formed during the reaction, nitrogen oxide (NO) is highly effective for inhibition of polymerization fouling.

4 Claims, No Drawings

INHIBITION OF POLYMERIZATION FOULING DURING DISTILLATION OF MONOMERS IN THE PRESENCE OF SULFUR OXIDES

BACKGROUND OF THE INVENTION

1. Field of the Invention

The present invention relates to a method for inhibiting the polymerization of acrylic acid and monomeric acrylates during the distillation thereof, and more particularly to the use of nitric oxide (NO) as an inhibitor in the distillation of acrylic acid and ethyl acrylate when oxides of sulfur are present.

2. Description of the Prior Art

Processes for the production of ethyl acrylate by the interaction of acrylic acid with ethylene in the presence of a sulfuric acid catalyst are well known. By way of example, see U.S. Pat. No. 3,703,539, issued Nov. 21, 1972, to DiLiddo; U.S. Pat. No. 3,539,621, issued Nov. 10, 1970, to Cipollone et al; and U.S. Pat. No. 3,894,076, issued July 8, 1975, to Van Duyne et al. In these and other prior art processes, the reaction is believed to involve the formation of intermediate sulfates from the reaction of ethylene with sulfuric acid wherein the sulfates further react with acrylic acid to form ethyl acrylate. To provide a product mixture in good overall yields with high carbon efficiencies, the reaction mixture is sent to a distillation train where the mixture is distilled to obtain liquid ethyl acrylate with unreacted ethylene, acrylic acid and sulfuric acid being recycled to the reactor. During distillation of the acrylate monomer, polymer formation and fouling are exacerbated due to the presence of oxides of sulfur such as sulfur dioxide or sulfur trioxide, which are derived from the sulfuric acid catalyst used in the ethylation reaction of ethylene with acrylic acid. This is a particularly serious problem in the recovery of ethyl acrylate since ethyl acrylate and acrylic acid are flashed from "black acid," the sulfuric acid medium from the ethylator, and the vent of the distillation recovery column will contain from 10 to 20 mol % of sulfur dioxide (corresponding to 0.4 to 0.8 wt. % of the ethyl acrylate product). Although it would be expected that polymer fouling would be inhibited by commonly used inhibitors such as phenothiazine, hydroquinone, p-methoxyphenol and the like, fouling during the distillation of acrylate monomers is exacerbated by the presence of sulfur dioxide.

Various inhibitors have been suggested for inhibiting polymerization during the distillation of acrylic acid and acrylate monomers. U.S. Pat. No. 2,741,583 to Vaughn et al discloses the use of alkali metal nitrites, such as sodium nitrite, or a mixture of nitrogen oxides as obtained by the action of an acid on such a nitrite, as polymerization inhibitors during the distillation of methyl or ethyl acrylates. British Patent GB No. 1,265,419 discloses a method for minimizing polymerization of acrylic acid during distillation thereof by distilling the acrylic acid in the presence of nitric oxide in the gas phase and phenothiazine in the liquid phase. U.S. Pat. No. 4,210,493 discloses the use of aliphatic and aromatic C- nitroso compounds, such as t-nitrosobutane and nitrosobenzene, to inhibit polymerization of acrylic and methacrylic acids during their preparation, purification and storage. In U.S. Pat. No. 4,542,231, nitric oxide is disclosed to prevent undesired or premature polymerization of ethylenically unsaturated organic monomer products such as acrylic acid.

SUMMARY OF THE INVENTION

The present invention is an improvement in a process for the production of ethyl acrylate from ethylene and acrylic acid utilizing a sulfuric acid catalyst wherein the reaction products, which contain oxides of sulfur, especially sulfur dioxide derived from the sulfuric acid catalyst, are distilled in the presence of nitric oxide (NO). While the use of nitric oxide as a polymerization inhibitor has been known in the prior art, it has been found unexpectedly that this type of inhibitor is effective in the distillation of acrylic acid/acrylate ester reaction mixtures containing sulfur dioxide.

DESCRIPTION OF THE INVENTION

In a representative process for producing ethyl acrylate according to the invention, ethylene and substantially anhydrous sulfuric acid medium are sprayed and mixed in the top portion of a reactor tower. The sulfuric acid medium comprises sulfuric acid residue or bottoms from a product recovery distillation tower together with make-up sulfuric acid. The sulfuric acid residue, referred to in the industry as "black acid," is a mixture of various compounds and contains sulfuric acid, intermediate sulfates from the reaction of ethylene and sulfuric acid, unreacted acrylic acid, small amounts of ethyl acrylate, and various other compounds. The main reaction occurring in the reactor tower is the liquid phase reaction of ethylene-enriched liquid with sulfuric acid to give various intermediate sulfate compounds, such as ethyl hydrogen sulfate and diethyl sulfate, which react with acrylic acid to form ethyl acrylate. Mixing of the reaction mixture is achieved by mechanical stirring or by recycle of reaction products. Temperature in the reaction tower is maintained within the range of about 100° C. to about 150° C. and usually about 110° C. to 130° C. The pressure should be maintained within the range of about 100 to 300 psig, preferably about 130 to 200 psig. The liquid phase reaction is carried out for a period of time sufficient to achieve substantial completion, at least 90% conversion of ethylene, acrylic acid and sulfuric acid to ethyl acrylate.

Reaction products withdrawn from the reactor tower are sent to a purification train comprising a recovery distillation tower, light ends distillation tower and finishing tower, all of which are of conventional design. In the recovery distillation tower, products withdrawn from the reactor tower are introduced through a pressure reduction valve and maintained under vacuum by conventional means so that the pressure is less than about 500 mm of mercury absolute. The still pot temperature is maintained within the range of about 100° C. to 170° C., preferably 100° C. to 130° C., and the still head temperature within the range of about 28° C. to 45° C., preferably about 30° C. to 40° C. A vacuum is maintained in the recovery column at reduced pressures less than atmospheric so that the pressure is within the range of 300 to 450 mm of mercury absolute. The distillation section of the recovery distillation tower is of conventional design and may contain packing, sieve type trays or dual flow trays. The distillation section will contain an equivalent of at least four theoretical trays. The residence time of the reaction products in the base of the distillation tower should be as low as possible because at temperatures required in the reboiler for vaporization some polymerization may occur. It is desirable to have a feed stream lean in acrylic acid being fed to the recovery distillation tower since this will result in less polymer formation.

I have found that the addition of NO is unexpectedly beneficial when purifying ethyl acrylate/acrylic acid mixtures containing sulfur oxides as produced in the above process. This inhibitor is added to the one or more of the distillation towers used for recovery and purification. Typical polymerization inhibitors such as hydroquinone, phenothiazine, p-methoxyphenol, benzoquinone and the like, although adequate to inhibit polymerization in columns containing no $SO_2$, will not effectively inhibit fouling when these additives are added to a column containing $SO_2$. The NO polymerization inhibitor can be introduced to the recovery distillation tower, the light ends distillation tower or finishing distillation tower in any part of the purification train. As an example, the inhibitor can be added to the recovery distillation tower from which it may be carried with the product through various finishing distillation towers, and thence into the residue of the final distillation tower.

The nitric oxide useful for the present invention may be added from a commercial source of the gas; may be generated externally to the reaction system, as for example from sodium nitrite in the presence of a mineral acid; or in situ, in the reaction system, as for example by the addition of a nitric oxide releasing agent, i.e. a metal nitrite, an N-nitroso compound, or the like.

Light ends of the reactor product, comprising mainly product ethyl acrylate and other reaction products, are removed overhead from the recovery distillation tower and passed to a light ends distillation tower of conventional distillation design. Unreacted ethylene is vented from the recovery distillation tower and may be disposed of or recycled to the reactor as desired. The bottoms product from the light ends distillation tower is a partially purified ethyl acrylate product which is passed to a finishing distillation tower where a substantially pure ethyl acrylate product is recovered by fractionation. The residue from the finishing distillation tower can be recycled to the reactor tower or a portion thereof sent to a wiped-film evaporator for recovery of organic products such as ethyl acrylate and acrylic acid.

To achieve improvement in the process for producing ethyl acrylate as described above, a small amount of nitric oxide is added to the ethyl acrylate recovery and/or light ends distillation tower in amounts ranging from 100 to 500 parts per million, preferably 150 to 400 parts per million, based on the total amount of ethyl acrylate/acrylic acid mixture introduced to the recovery tower.

The presence of sulfur dioxide in the recovery distillation column actually promotes polymer formation in the recovery distillation column and may even lead to the formation of sulfur dioxide/ethyl acrylate copolymers. Polymer foulant removed from such columns has been found to contain significant quantities of sulfur by analysis. The amount of sulfur oxides, based on the feed materials, will generally range from 0.4 to 0.8 wt. %. Under the conditions of temperature and pressure used in this column, it would be expected that inhibition of polymer fouling would be straightforward by using conventional inhibitors such as phenothiazine, hydroquinone, and the like. To the contrary, it has been experienced that this column fouls rapidly and severely. By means of the present invention, nitric oxide (NO) has been found highly effective for inhibiting polymer formation in the presence of oxides of sulfur, e.g., sulfur dioxide contaminant.

EXAMPLE 1

The reboiler of a 15-tray, 2-inch Oldershaw column is fed with a mixture of ethyl acrylate containing 9 wt. % acrylic acid and 0.71 wt. % sulfur dioxide at a feed rate of 42.1 gm/min. Nitric oxide (NO) is also fed to the column at a rate of 0.0088 gm/min for vapor phase inhibition. This corresponds to an NO concentration of 209 wt. ppm in the feed. The column is operated at 400 mm HgA with the base temperature at 85° C. The overhead distillate rate is 48.7 wt. % of the feed, the ratio of boilup to feed is 1.2 and the reflux ratio is 1.6. The NO allows the column to be operated for a duration of more than 3 hours without any signs of fouling.

EXAMPLE 2

In contrast to Example 1, using 200 ppm of phenothiazine inhibitor without NO, under the conditions of Example 1, significant fouling occurs.

What is claimed is:
1. In a method for production of ethyl acrylate comprising the steps of:
   (1) reacting ethylene and acrylic acid in the presence of sulfuric acid to form reaction products comprising ethyl acrylate, sulfuric acid residue, sulfur dioxide, unreacted ethylene and acrylic acid;
   (2) distilling said reaction products at reduced pressure less than atmospheric to obtain a crude ethyl acrylate product and a sulfuric acid residue; the improvement which comprises carrying out said distillation in the present of 100 to 500 parts per million of nitric oxide.
2. The method of claim 1 wherein the amount of nitric oxide is present in the amount of 150 to 400 parts per million.
3. The method of claim 1 wherein the amount of sulfur dioxide present in the reaction products is about 0.4 to 0.8 wt. %.
4. The method of claim 1 wherein the distillation is carried out at a temperature of 100° C. to 170° C. under a pressure of 300 to 450 mm of mercury absolute.

* * * * *